(12) United States Patent
Drucker et al.

(10) Patent No.: US 6,387,110 B1
(45) Date of Patent: May 14, 2002

(54) COATING FOR SURGICAL BLADES

(75) Inventors: Karen Drucker, Danville; Peter Cesarini, Londonderry, both of NH (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/338,337

(22) Filed: Jun. 23, 1999

(51) Int. Cl.[7] ............................................... A61B 17/32
(52) U.S. Cl. ........................................ 606/170; 606/180
(58) Field of Search ................................ 606/167, 166, 606/168, 169, 170, 171–180, 79, 80; 427/239, 230

(56) References Cited

U.S. PATENT DOCUMENTS

| | | | |
|---|---|---|---|
| 3,941,903 A | * 3/1976 | Tucker, Jr. | 427/190 |
| 3,950,141 A | 4/1976 | Roemer | 29/196.2 |
| 4,678,459 A | 7/1987 | Onik et al. | 604/22 |
| 4,686,982 A | 8/1987 | Nash | |
| 4,923,441 A | 5/1990 | Shuler | 604/22 |
| 5,160,318 A | 11/1992 | Shuler | 604/22 |
| 5,269,798 A | 12/1993 | Winkler | 606/170 |
| 5,324,301 A | 6/1994 | Drucker | 606/180 |
| 5,413,756 A | 5/1995 | Sahu | 420/472 |
| 5,607,435 A | * 3/1997 | Sachdeva et al. | 606/139 |
| 5,630,826 A | * 5/1997 | Sastri | 606/170 |
| 5,759,185 A | * 6/1998 | Grinberg | 606/80 |
| 5,782,795 A | 7/1998 | Bays | 604/22 |
| 5,925,039 A | * 7/1999 | Landingham | 606/41 |

OTHER PUBLICATIONS

Metals Handbook 9th edition, ASM Committee on Sliding Bearings, "Materials for Sliding Bearings", vol. 3., pp. 802–822, 1980.

* cited by examiner

*Primary Examiner*—David O. Reip
(74) *Attorney, Agent, or Firm*—Fish & Richardson P.C.

(57) ABSTRACT

A surgical blade includes an elongate outer tubular member and an elongate inner member movably received within the outer member. The inner member has a distal cutter positionable adjacent a distal opening in the outer member. A coating of copper or alloys or mixtures of copper and one or more other elements is on a portion of the outer surface of the inner member, the inner surface of the outer member, or both. The outer and inner members are formed from stainless steel, e.g, soft stainless steel. A method of cutting tissue, e.g., hard tissue such as bone, includes providing a surgical blade having an inner member and/or an outer member coated with copper or alloys or mixtures of copper and one or more other elements, placing the surgical blade against the tissue, and driving the inner member to cut the tissue.

29 Claims, 1 Drawing Sheet

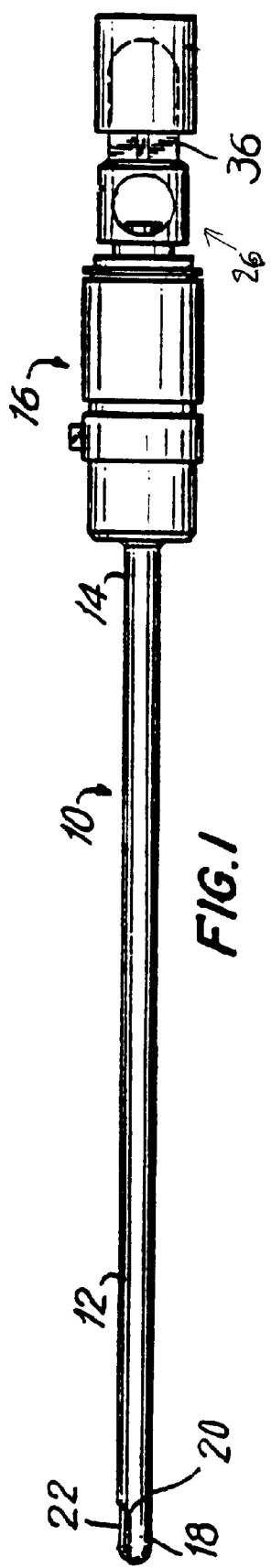
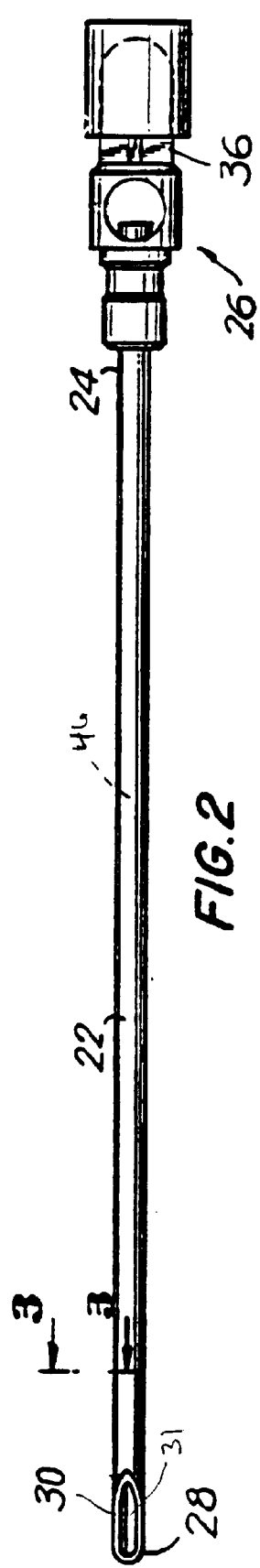
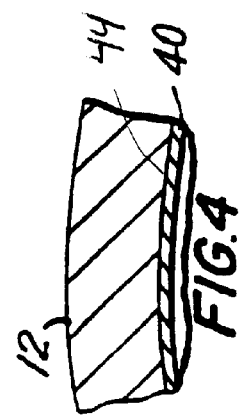

COATING FOR SURGICAL BLADES

BACKGROUND OF THE INVENTION

The present invention relates to surgical blades and, more particularly, to endoscopic surgical blades having elongate, inner and outer tubular members with distal ends cooperating to cut or resect bodily tissue.

Endoscopic surgical blades typically have an elongate outer tubular member terminating at a distal end having an opening in the side wall and/or the end wall to form a cutting port or window and an elongate inner tubular member coaxially disposed in the outer tubular member and having a distal end disposed adjacent the opening in the distal end of the outer tubular member. The distal end of the inner tubular member has a surface or edge for engaging tissue via the opening in the distal end of the outer tubular member and in many cases cooperates with the opening to shear or cut tissue. The inner tubular member is typically rotatable relative to the outer tubular member.

The distal end of the inner tubular member can have various configurations dependent upon the surgical procedure to be performed. The opening in the distal end of the outer tubular member is configured to cooperate with the particular configurations of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to herein generically as "cutting blades or edges." Cut tissue is typically aspirated through the lumen of the inner tubular member.

The inner and outer members are typically formed from electropolished stainless steel. It is known to coat the surfaces of the members with a layer of silver, gold, tin-nickel alloy, or titanium nitride to act as a bearing surface between the outer and inner members.

SUMMARY OF THE INVENTION

According to one aspect of the invention, a surgical blade includes an elongate outer tubular member and an elongate inner member movably received within the outer member. The inner member has a distal cutter positionable adjacent a distal opening in the outer member. A coating from the group consisting of copper and alloys or mixtures of copper and one or more other elements is on a portion of the outer surface of the inner member, the inner surface of the outer member, or both.

Embodiments of this aspect of the invention may include one or more of the following features.

The coating is white bronze, an alloy of copper, tin and zinc. Preferably about 55–60% copper, 20–25% tin, and 15–20% zinc. The outer and inner members are formed from stainless steel, e.g, soft stainless steel such as 300 series stainless steel.

The coating is in a region of the distal opening of the outer tubular member, a region of the distal cutter of the inner member, or both. The coating is along substantially an entire length of the inner surface of the outer tubular member, the outer surface of the inner member, or both.

The inner member defines a lumen. The inner member is received within the outer tubular member for rotation therein. Alternatively, the inner member is received within the outer tubular member for axial, reciprocating motion therein.

The clearance between a distal region of the outer member and a distal region of the inner member prior to applying the coating is in a range of about 0.0001" to 0.002", preferably about 0.00075" to 0.00175". The thickness of the coating is in a range of about 0.00002" to 0.0005".

According to another aspect of the invention, a method of cutting tissue includes providing a cutting blade having a portion of the outer surface of the inner member, the inner surface of the outer members, or both coated with a coating from the group consisting of copper and alloys or mixtures of copper and one or more other elements, placing the cutting blade against the tissue, and driving the inner member to cut the tissue.

Embodiments of this aspect of the invention may include one or more of the following features.

The outer and inner members are formed from stainless steel, e.g., soft stainless steel. The clearance between a distal region of the outer member and a distal region of the inner member prior to applying the coating is in a range of about 0.0001" to 0.002", preferably about 0.00075" to 0.00175". The coating has a thickness in a range of about 0.00002" to 0.0005". The method includes cutting hard tissue such as bone. The step of driving includes rotating the inner member within the outer member. The blade is sterilizable by autoclaving.

According to another aspect of the invention, a method of making a surgical blade includes providing the outer tubular member and the inner member, and coating the inner surface of the outer tubular member, the outer surface of the inner tubular member, or both with copper or alloys or mixtures of copper and one or more other elements.

Advantages of the invention may include one or more of the following: The copper or copper alloy coating limits shedding. The coating provides good performance of the surgical blade particularly at high speeds, and also provides good performance of the surgical blade under high loads, e.g., when cutting bone. The coating is available in alloys which have oxidation resistant properties to limit tarnishing. The coating can be deposited by conventional electroplating techniques in an economical manner, can be sterilized by conventional processing such as gamma radiation and autoclaving, without changing color, and is non-cytotoxic.

Other features and advantages of the invention will be apparent from the following detailed description.

BRIEF DESCRIPTION OF THE DRAWINGS

FIG. 1 is a side elevation of a surgical cutting instrument according to the present invention.

FIG. 2 is a side elevation of an inner tubular member of the surgical cutting instrument of FIG. 1;

FIG. 3 is a detail view in section, in enlarged scale, taken along lines 3—3 of FIG. 2; and FIG. 4 is a detail view, similar to FIG. 3, of another embodiment of the present invention.

DESCRIPTION OF THE PREFERRED EMBODIMENTS

Referring to FIG. 1, a surgical blade 10 includes an elongate tubular outer member 12 having a proximal end 14 fixed to an outer hub 16 and a distal end 18 defining an opening 20 forming a cutting port or window. Referring also to FIG. 2, an elongate tubular inner member 22 is rotatably received in outer tubular member 12. Inner member 22 has a proximal end 24 fixed to an inner hub 26, and a distal end 28 having a cutting edge 30. Cutting edge 30 defines an aperture 31 communicating with a lumen 46 defined in inner member 22. Inner hub 26 includes a tang 36 adapted to be driven by an electric motor (not shown) to rotate inner member 22. Alternatively, inner member 22 undergoes axial, reciprocating motion within outer member 12. When blade 10 is assembled, inner hub 26 is received in outer hub 16 and cutting edge 30 is positioned adjacent opening 20 of outer member 12.

Outer member 12 and inner member 22 are formed from electropolished stainless steel, e.g., hardened stainless steel such as 400 series stainless steel, or soft stainless steel such as 300 series stainless steel. The distal ends 18, 28 of outer and inner members 12, 22, respectively, are spaced close together, e.g., with a clearance within about 0.0001" to 0.002", preferably about 0.00075" to 0.00175", in order to provide optimum cutting action.

Referring to FIG. 3, a bearing surface coating 40 of copper, an alloy of copper and one or more other elements, e.g., bronze or white bronze (a 55–60% copper, 20–25% tin, and 15–20% zinc alloy passivated to resist oxidation); or a plated mixture of copper and one or more other elements where the mixture does not constitute a molecular compound, (e.g., a mixture of 55–60% copper, 20–25% tin, and 15–20% zinc), is electroplated on an outer surface 42 of inner member 22.

For example, a coating of copper sulfate is first plated on outer surface 42 followed by plating in a white bronze bath. Prior to plating with the copper sulfate, outer surface 42 is degreased, electrocleaned anodically using an alkaline cleaner, and rinsed. Outer surface 42 is then simultaneously activated and plated under the following conditions: 0.4 g copper sulfate ($CuSO_4, 5H_2O$), 1 L hydrochloric acid (conc), at room temperature, for 1–5 minutes, with nickel anode material, and cathode CD 40–60 ASF. Outer surface 42 is rinsed and then plated in the white bronze bath.

Preferably, coating 40 runs substantially the full length of outer surface 42 of inner member 22 from distal end 28, including cutting edge 30, to proximal end 24, and over the full circumference of the inner member. However, it may be sufficient to apply coating 40 only at the distal ends of the members if there is sufficient clearance along the remainder of the members to prevent contact between the remainder of the members during use. It may be sufficient to apply coating 40 less than over the full circumference of the inner member, e.g., as stripes.

Coating 40 preferably has a thickness of about 0.00002" to 0.0005" such that the outer diameter of inner tubular member 22 is substantially the same as the inner diameter of outer tubular member 12, with the coating 40 engaging the inner surface of the outer tubular member during use to form a bearing surface. As shown in FIG. 4, coating 40 may be applied to an inner surface 44 of outer member 12 or to both outer surface 42 of inner member 22 and inner surface 44 of outer member 12.

In operation, inner member 22 is rotatably driven in outer member 12 (up to high speeds in the range of about 1,000 rpm to 10,000 rpm) such that cutting edge 30 engages body tissue via cutting port or window 20. Cut tissue is aspirated through lumen 46 via aperture 31.

In the absence of a surface coating 40, shedding (the removal of material from the facing surfaces 44, 42 of the outer and inner members 12, 22, respectively) may occur due to contact between outer and inner members 12, 22. This is particularly problematic when outer and inner members 12, 22 are formed from soft stainless steel, are closely spaced, and are subjected to high loads encountered when using cutting blade 10 to cut hard tissue such as bone and cartilage. The load on the blade tends to cause bending of the members, increasing the contact force between the members and thus increasing the shedding. The bearing characteristics of a coating of copper or copper alloy are sufficient to reduce wear of surfaces 40, 42, when cutting blade 10 is subjected to high load, limiting shearing, galling and seizing of blade 10. Furthermore, use of white bronze as the coating material limits tarnishing of the coated surface.

Cutting blade 10 can be sterilized by conventional techniques such as gamma radiation and autoclaving, without changing the color of coating 40. Opening 20 can have any desired configuration to cooperate with the configuration of the cutting edge or edges on the distal end of the inner tubular member so as to form trimmers, meniscus cutters, end cutters, side cutters, full radius cutters, synovial resectors, whiskers, open end cutters, arthroplasty burrs, slotted whiskers, tapered burrs, oval burrs, punch forceps and the like. The surgical cutting instrument of the present invention can have any desirable hub configuration to be utilized with any drive system or handpiece capable of rotating or reciprocating an elongate inner tubular member within an elongate outer tubular member to cut or otherwise engage body tissue at the distal end.

Other embodiments are within the scope of the following claims.

For example, instead of defining a lumen, inner member 22 can be solid. Inner member 22 can be in the form of an auger.

What is claimed is:

1. A method of cutting soft tissue and hard tissue, the method comprising:
   providing a surgical blade including
      an elongate outer tubular member having an inner surface and defining a distal opening,
      an elongate inner member having an outer surface, the elongate inner member being movably received within the outer tubular member, the elongate inner member including a distal cutter positionable adjacent the distal opening in the outer tubular member to permit the cutter to engage tissue through the distal opening, at least one of the inner and outer members being formed of soft stainless steel, and
      a coating selected from the group consisting of copper and alloys or mixtures of copper and one or more other elements on a portion of the outer surface of the inner tubular member, the inner surface of the outer tubular member, or both,
   placing the cutting blade against soft tissue or hard tissue, and
   driving the inner member to cut the tissue.

2. The method of claim 1 wherein the outer tubular member and the inner tubular member are formed from stainless steel.

3. The method of claim 2 wherein the stainless steel is soft stainless steel.

4. The method of claim 2 wherein the soft stainless steel is 300 series stainless steel.

5. The method of claim 1 wherein providing the surgical blade includes providing the inner and outer members with a clearance between a distal region of the outer member and a distal region of the inner member prior to applying the coating in a range of about 0.0001" to 0.002".

6. The method of claim 5 wherein the clearance is about 0.00075" to 0.00175".

7. The method of claim 1 wherein providing the surgical blade includes providing the coating with a thickness in a range of about 0.00002" to 0.0005".

8. The method of claim 1 wherein driving the inner member includes rotating the inner member within the outer member.

9. The method of claim 1 wherein providing the surgical blade includes providing the surgical blade sterilized by autoclaving.

10. A method of making a surgical blade for cutting soft tissue and hard tissue, the method comprising:

providing an elongate outer tubular member having an inner surface and defining a distal opening, providing an elongate inner member having an outer surface, the elongate inner member being movably received within the outer tubular member, the elongate inner member including a distal cutter positionable adjacent the distal opening in the outer tubular member to permit the cutter to engage tissue through the distal opening, at least one of the inner and outer members being formed of soft stainless steel, and coating the inner surface of the outer tubular member, the outer surface of the inner tubular member, or both with copper or alloys or mixtures of copper and one or more other elements.

11. A method of forming a blade for cutting hard tissue, the method comprising:

providing an inner member and an outer tubular member, at least one of the inner and outer members being formed from soft stainless steel, coating a portion of an outer surface of the inner member, an inner surface of the outer tubular member, or both with a composition selected from the group consisting of copper and alloys or mixtures of copper and one or more other elements such that the blade can be used to cut hard tissue.

12. The method of claim 11 wherein the composition comprises white bronze.

13. The method of claim 12 wherein the white bronze is an alloy of copper, tin, and zinc.

14. The method of claim 13 wherein the white bronze comprises about 55–60% copper, 20–25% tin, and 15–20% zinc.

15. The method of claim 11 wherein both the outer tubular member and the inner member are formed from stainless steel.

16. The method of claim 15 wherein the stainless steel is soft stainless steel.

17. The method of claim 16 wherein the soft stainless steel is 300 series stainless steel.

18. The method of claim 11 wherein the portion is in a region of a distal opening of the outer tubular member, a region of a distal cutter of the inner member or both.

19. The method of claim 11 wherein the portion is along substantially an entire length of the inner surface of the outer tubular member, the outer surface of the inner member, or both.

20. The method of claim 11 wherein the inner surface of the inner member defines a lumen.

21. The method of claim 11 wherein the inner member is received within the outer tubular member for rotation therein.

22. The method of claim 11 wherein the inner member is received within the outer tubular member for axial, reciprocating motion therein.

23. The method of claim 11 wherein a clearance between a distal region of the outer member and a distal region of the inner member prior to applying the coating is in a range of about 0.0001" to 0.002".

24. The method of claim 23 wherein the clearance is about 0.00075" to 0.00175".

25. The method of claim 11 wherein a thickness of the coating is in a range of about 0.00002" to 0.0005".

26. The method of claim 11 wherein the hard tissue comprises bone.

27. The method of claim 11 wherein the hard tissue comprises cartilage.

28. The method of claim 11 wherein both the inner and outer members are formed from soft stainless steel.

29. A method of cutting hard tissue, the method comprising:

providing a surgical blade having an inner member and an outer tubular member, at least one of the inner and outer members being formed from soft stainless steel, a portion of an outer surface of the inner member, an inner surface of the outer tubular member, or both being coated with a composition selected from the group consisting of copper and alloys or mixtures of copper and one or more other elements, placing the blade against hard tissue, and cutting hard tissue with the blade.

* * * * *